United States Patent [19]

Mikkelsen

[11] Plant 4,002

[45] Jan. 4, 1977

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 653,019

[22] Filed: Jan. 28, 1976

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Donald D. Jeffery

CLAIM

A new and distinct form of impatiens plant known by the cultivar name Fanfare and particularly characterized by the combined characteristics of distinctive deep green foliage with a very clean cut interior yellow variegation; self-branching habit presenting many points of flowering; flower diameter of 3 cm. to 4 cm.; medium red flower color in winter, with the interior of the petals being light red to pink, with the summer flower color being light red with the interior fading to nearly white; superior outdoor growth habit in full sunlight; normal rooting habit; good durability, and above average production of number of cuttings at each node.

1 Drawing Figure

IMPATIENS PLANT

The present invention relates to a new and distinctive cultivar of New Guinea Impatiens plant, referred to by the cultivar name Fanfare and botanically known as Impatiens. The new cultivar was developed by me through controlled breeding by crossing the seed parent identified by plant selection No. 349583 from New Guinea with the pollen parent identified by plant selection No. 354261 from New Guinea. Asexual reproduction of terminal or stem cuttings has shown that the unique features of this new impatiens cultivar are stabilized and are reproduced true to type in successive propagations. The following characteristics distinguish Fanfare from both its parent varieties and other cultivated impatiens of this type known and used in the floriculture industry:

1. Its distinctive deep green foliage with a very clean cut interior yellow variegation. The foliage is crisp and glabrous. Leaves are arranged in whorls at the nodes.
2. Plant is self branching thereby presenting many points of flowering; Fanfare has been observed to flower continuously for at least seven months, April through October.
3. Flower diameter is 3 cm. to 4 cm. and flower color is medium red in winter with light red to pink interior of the petals, to light red in summer with interior fading to nearly white. The flower size is considered small for New Guinea impatiens.
4. The new cultivar grows extremely well outdoors in Ohio in full sunlight. If soil moisture is adequately maintained the foliage does not burn. Plants 9 inches tall outside in June were approximately 18 to 20 inches tall by October.
5. Rooting of cuttings is near normal for New Guinea impatiens, taking approximately 10 days to develop roots 5–6 mm. long when propagating media is 22° C.
6. The new cultivar is quite durable as demonstrated in its good shipping qualities during extreme high temperature periods of the summer months in Ohio.
7. Seed produced by self pollination do not come true to type.
8. Stock plants of the new cultivar produce above average numbers of cuttings at each node; rooting is fast and dependable; very little losses from soft rot organisms.

The accompanying colored photograph illustrates the overall appearance of this cultivar taken as a face view of the plant and showing the colors as true as it is reasonably possible to obtain in a colored reproduction of this type.

The following is a detailed description of my new impatiens cultivar based on plants produced under commercial practices in greenhouse and field plantings at Ashtabula, Ohio. It should be noted that Impatiens, being very succulent, can alter their growth patterns very quickly with varying environmental conditions. Color references in the following description are to the Royal Horticultural Society Colour Chart except where general terms of ordinary dictionary significance are used.

Parentage: A controlled pollination of plant selection No. 349583 as the seed parent crossed with plant selection No. 354261 as the pollen parent.

Propagation:

A. *Type cutting.*—Either terminal or stem cuttings.
B. *Time to root (summer).*—6 to 10 days at 22° C. Time to root (winter): 8 to 12 days at 22° C.
C. *Rooting habit.*—Very rapid, profuse, dendritic.

PLANT DESCRIPTION

A. Form: Upright self-branching herb or low growing shrub. Plant develops quite symmetrically.
B. Habit of growth: Medium to fast growing, upright, self-supporting when given sufficient area to develop without crowding.
C. Foliage: Beginning as opposite to whorls of three up to five leaves at each node.
   1. *Size.*—5–6 cm. wide by 12–14 cm. long, with a rather short petiole on mature leaves measuring 10–15 mm. long.
   2. *Shape.*—Symmetrically elliptical, tip acuate, base attenuate, veining pinnate.
   3. *Texture.*—Glabrous, firm.
   4. *Margin.*—Very shallow serrated to nearly entire.
   5. *Color.*—Young Foliage, top side—green 137B-C/yellow darker than 20A. underside—green near 146A/diffused yellow. Mature Foliage, top side—green 137B-C/yellow between 14C and 13B. underside—green near 146A/lighter than 14C.

6. *Venation.*—Recessed upper surface, protruding lower surface, color of veins deep pink to light red.

FLOWERING DESCRIPTION

A. Flowering habits: Individual flowers open successively around the whorl, each lasting several days, the last generally still being in flower as the first flower in the next whorl begins to develop.

B. Natural flowering season: Indeterminate at the present time. Flowering occurs in all seasons, at various temperatures and day lengths.

C. Flower bud description: Covered with four sepals; the lower sepal developing a spur 5–6 cm. in length and having the same color as the flower pedicel, red 53-B.

D. Flowers borne: On individual pedicels in a whorl corresponding to the number of leaves in the whorl at each node. Pedicels up to 6–7 cm. long.

E. Quantity of flowers: Same number as the leaves in the whorl.

F. Petals:

1. *Shape.*—irregular tending to be oblong with a terminal notch.
2. *Color.*—Top side in winter when opening, irradescent, more red than 52-B, fading to red 55-C; top side in summer near 49-A; underside, nearly red 38-A.
3. *Number of petals.*—five; top isolated; lower four overlapping.
4. *Size of petals/flowers.*—petals 1.5 cm. to 2 cm.; flower diameter up to 4 cm.

G. Reproductive Organs:

1. *Stamens.*—One in number, which drops off when ripe.
   a. Anther shape: Hooded over pistil, color exterior red, interior white.
   b. Pollen color: White
2. *Pistils:*
   a. Stigma shape: Irregular, color white.
   b. Style color: White.
   c. Ovaries: One in number, size 5–6 mm., green in color.

Disease resistance: Immune to mildew, susceptible to botrytis, pythium and other soft rot organisms when under reduced light conditions in the winter months.

Other important characteristics that further distinguish Fanfare from other impatiens cultivars are as follows. When grown with other impatiens plants infected with common red spider mite, Fanfare shows very high level of resistance to that organism, an important factor in using impatiens for outdoor plantings. In addition, Fanfare is quite durable as an indoor pot plant, being very decorative with its foliage alone.

I claim:

1. A new and distinct form of impatiens plant known by the cultivar name Fanfare and particularly characterized by the combined characteristics of distinctive deep green foliage with a very clean cut interior yellow variegation; self-branching habit presenting many points of flowering; flower diameter of 3 cm. to 4 cm.; medium red flower color in winter, with the interior of the petals being light red to pink, with the summer flower color being light red with the interior fading to nearly white; superior outdoor growth habit in full sunlight; normal rooting habit; good durability, and above average production of number of cuttings at each node.

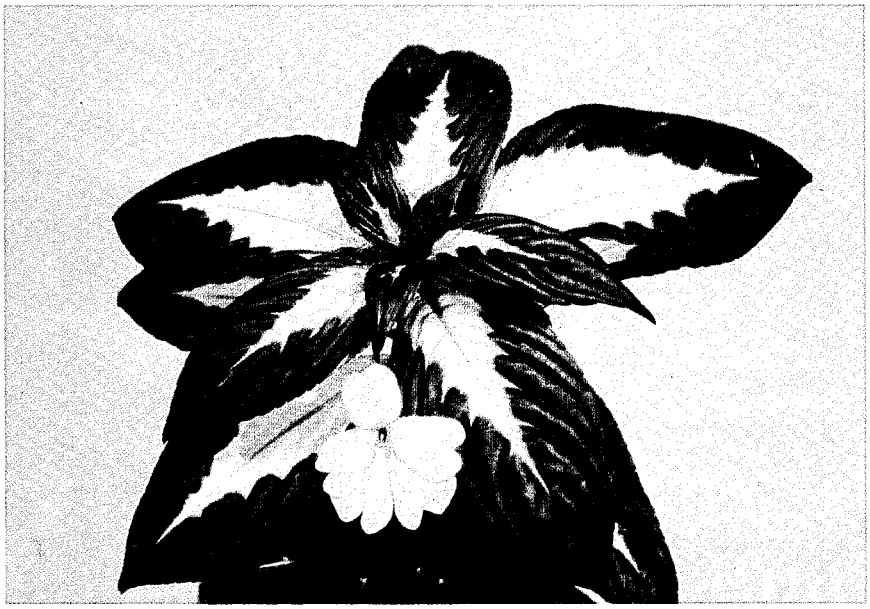

* * * * *